(12) United States Patent
Sakai et al.

(10) Patent No.: US 7,856,730 B2
(45) Date of Patent: Dec. 28, 2010

(54) INTERNAL DIAMETER MEASUREMENT DEVICE

(75) Inventors: Masato Sakai, Tokyo (JP); Masatoshi Tonomura, Tokyo (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 12/352,070

(22) Filed: Jan. 12, 2009

(65) Prior Publication Data
US 2009/0178289 A1  Jul. 16, 2009

(30) Foreign Application Priority Data
Jan. 15, 2008 (JP) .............................. 2008-006282

(51) Int. Cl.
*G01B 13/10* (2006.01)

(52) U.S. Cl. ........................ 33/543.1; 33/542

(58) Field of Classification Search .................. 33/543, 33/542, 555.1, 555.2; 606/533, 18, 115–117, 606/587
See application file for complete search history.

(56) References Cited

U.S. PATENT DOCUMENTS

| | | | | | |
|---|---|---|---|---|---|
| 4,643,192 | A | * | 2/1987 | Fiddian-Green | ............ 600/366 |
| 5,171,299 | A | * | 12/1992 | Heitzmann et al. | ........... 606/191 |
| 5,902,308 | A | * | 5/1999 | Murphy | ....................... 606/108 |
| 6,010,511 | A | | 1/2000 | Murphy | |
| 6,146,357 | A | * | 11/2000 | Addis | ..................... 604/100.03 |
| 6,241,678 | B1 | * | 6/2001 | Afremov et al. | ............. 600/481 |
| 6,536,260 | B2 | * | 3/2003 | Williams | ...................... 600/18 |
| 7,007,396 | B2 | * | 3/2006 | Rudko et al. | ................... 33/512 |
| 7,476,203 | B2 | * | 1/2009 | DeVore et al. | .............. 600/587 |
| 7,476,235 | B2 | * | 1/2009 | Diederich et al. | ............ 606/192 |
| 2004/0010209 | A1 | * | 1/2004 | Sirokman | ..................... 600/587 |
| 2004/0059263 | A1 | | 3/2004 | DeVore et al. | |
| 2005/0010138 | A1 | * | 1/2005 | Mangiardi et al. | .......... 600/587 |
| 2006/0064039 | A1 | | 3/2006 | Griego et al. | |
| 2006/0155217 | A1 | * | 7/2006 | DeVore et al. | .............. 600/587 |
| 2008/0005916 | A1 | * | 1/2008 | Francis et al. | ................. 33/512 |
| 2009/0054805 | A1 | * | 2/2009 | Boyle, Jr. | ..................... 600/564 |

FOREIGN PATENT DOCUMENTS

| | | |
|---|---|---|
| JP | 2-44722 | 11/1990 |
| JP | 2000-292108 | 10/2000 |
| JP | 2005-214958 | 8/2005 |

OTHER PUBLICATIONS

European Search Report dated May 11, 2009 in corresponding European Application No. EP 09 00 0317 (English language).

* cited by examiner

*Primary Examiner*—Yaritza Guadalupe-McCall
(74) *Attorney, Agent, or Firm*—Ostrolenk Faber LLP

(57) ABSTRACT

The internal diameter measurement device is inserted into a cavity to measure its internal diameter. The internal diameter measurement device includes: a tubular sheath inserted into the cavity; a balloon which is provided on a distal end portion of the sheath, and is capable of expanding by supplying a fluid to an inner portion thereof; a linear reference member having a first end portion fixed to the distending portion or the distal end portion of the insertion portion, and a second end portion moving towards the distal end of the insertion portion in conjunction with the expansion of the distending portion; and a measuring portion which is provided in a proximal end portion of the insertion portion and is capable of confirming the position of the second end portion of the reference member. This internal diameter measurement device enables accurate measurement irrespectively of dimensions of a pipeline to be measured.

7 Claims, 7 Drawing Sheets

INTERNAL DIAMETER MEASUREMENT DEVICE

BACKGROUND OF THE INVENTION

1. Field of the Invention

The present invention relates to an internal diameter measurement device for measuring the internal diameter of a cavity. Priority is claimed on Japanese Patent Application No. 2008-6282, filed Jan. 15, 2008, the content of which is incorporated herein by reference.

2. Description of Related Art

Conventionally, an internal diameter measurement device is known which is inserted into a channel of various types of endoscopes for medical or industrial use, and then inserted into luminal organs such as the bronchial tubes or the esophagus, into gas piping or water piping, or into piping for machinery or equipment to thereby measure an internal diameter thereof (For example, refer to Patent Document 1: Japanese Examined Utility Model Application, Second Publication No. H2-44722).

Furthermore, an internal diameter measurement device is known which has a length measuring portion which expands and contracts in the radial direction and which can be coordinated with the action of an operating portion (For example, refer to Patent Document 2: Japanese Unexamined Patent Application, First Publication No. 2000-292108).

The internal diameter measurement device disclosed in Patent Document 1 is provided with a scale, both ends of which are connected by a wire, and which is provided at a distal end of an outer covering pipe such as a coil sheath. Dimensional measurements are performed using the scale.

SUMMARY OF THE INVENTION

An aspect of the present invention relates to an internal diameter measurement device which is inserted into a cavity to measure an internal diameter thereof, the internal diameter measurement device including: a tubular insertion portion inserted into the cavity; a distending portion which is provided on a distal end portion of the insertion portion, and is capable of expanding by supplying a fluid to an inner portion thereof; at least one linear reference member having a first end portion fixed to the distending portion or the distal end portion of the insertion portion, and a second end portion moving towards the distal end of the insertion portion in conjunction with the expansion of the distending portion; and a measuring portion which is provided in a proximal end portion of the insertion portion and is capable of confirming the position of the second end portion of the reference member.

In this internal diameter measurement device, when the distending portion expands up to the internal diameter of the cavity, the second end portion of the reference member displaces towards the distal end of the insertion portion together with an increase in the diameter of the distending portion caused by the expansion. Consequently, by confirming the amount of displacement of the reference member with the position of the second end portion by the measuring portion, it is possible to measure the internal diameter of the cavity.

The reference member may be inserted through an inner cavity of the insertion portion in a freely sliding manner in the axial direction. In this case, even when the insertion portion meanders inside the cavity, the reference member can reliably accompany with the insertion portion.

The reference member may include a marker which is provided in the vicinity of the second end portion and is capable of being visually confirmed in the measurement portion. In this case, it is possible that a user easily reads and confirms the displacement of the reference member in the measurement portion.

The second end portion of the reference member may be mounted to the measurement portion via a position adjustment member having elasticity. In this case, it is possible to set such that the second end portion of the reference member automatically returns to an initial position showing a zero measurement value when the distending portion contracts.

The distending portion may be mounted so as to encircle at least a portion of an outer periphery of the insertion portion. The reference member may project from the inner cavity of the insertion portion, and pass on an outer peripheral face of the distending portion along the axial direction of the insertion portion. The first end portion may be fixed to the insertion portion. In this case, the maximum diameter of the expanded distending portion is accurately reflected on the displacement amount of the reference member and thus highly accurate measurement is enabled.

The distending portion may expand in a spherical shape and be mounted so as to encircle at least a portion of an outer periphery of the insertion portion. The inner cavity of the insertion portion may have an opening into the inner portion of the distending portion. The first end portion of the reference member may project from the opening of the inner cavity and be fixed on an inner peripheral line of the distending portion at a central portion in the axial direction of the insertion portion. In this case, a high correlation is created between the diameter of the distending portion and the amount of displacement of the reference member and thus highly accurate measurement is enabled.

The reference member may be displaced towards the distal end of the insertion portion as a result of extension of the distending portion. In this case, highly accurate measurement is enabled since the diameter increase of the distending portion is more accurately reflected on the amount of displacement of the reference member.

DETAILED DESCRIPTION OF THE INVENTION

An internal diameter measurement device according to the first embodiment of the present invention will be described making reference to FIGS. 1 to 4.

Figure 1:
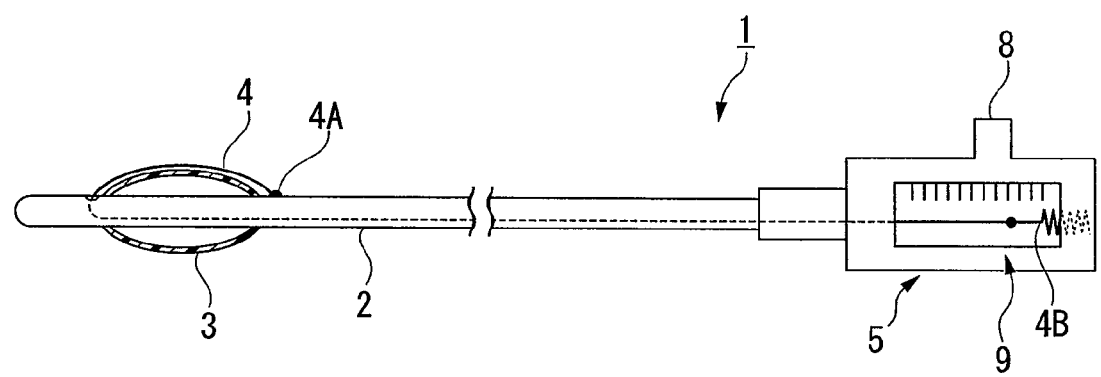
FIG. 1 depicts an internal diameter measurement device according to a first embodiment of the present invention.
Figure 2:
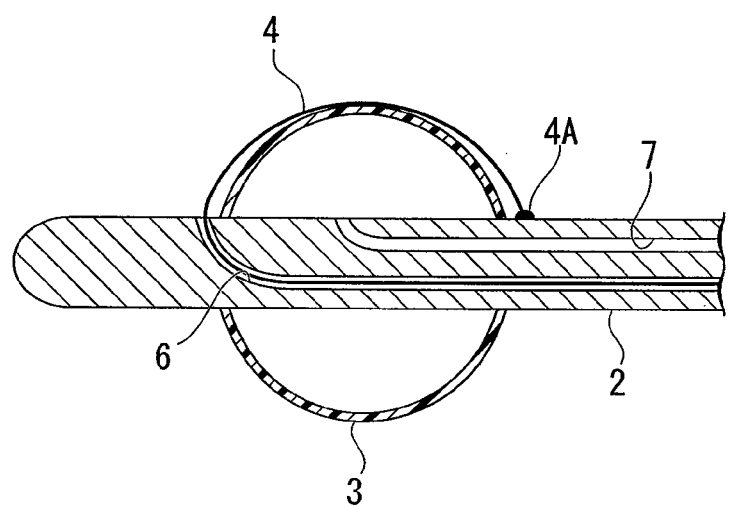
FIG. 2 is a sectional view of a distal end portion of the internal diameter measurement device.

FIG. 1 depicts an internal diameter measurement device 1 according to the present embodiment. FIG. 2 is a sectional view depicting the distal end portion of the internal diameter measurement device 1. As depicted in FIG. 1, the internal diameter measurement device 1 has a sheath (insertion portion) 2 inserted into a cavity which is the object of measurement, a balloon (distending portion) 3 mounted in a distal end portion of the sheath 2 so as to encircle an outer periphery of the sheath 2, a reference member 4 fixed in the distal end portion of the sheath 2, and an operating portion 5 mounted in the proximal end side of the sheath 2.

As depicted in FIG. 2, the sheath 2 has two cavities being a first lumen (inner cavity) 6 through which the reference member 4 is inserted, and a second lumen 7 for supplying a fluid to an inner portion of the balloon 3. The sheath 2 is preferably formed from a flexible material such as a resin, since good insertion is obtained even when the pipeline undergoes nosing or the like.

The balloon 3 is formed from a resin or the like and is adapted to expand in a spherical shape by supplying a fluid such as a liquid or a gas to the inner portion thereof through the second lumen 7.

The reference member 4 is formed from a linear material such a thread or a thin wire which tends not to expand or contract in the axial direction. The reference member 4 is inserted into the first lumen 6 in a freely sliding manner in the axial direction. The first lumen 6 has an opening positioned more toward the distal end of the sheath 2 than the balloon 3. A first end portion 4A of the reference member 4 projecting from the sheath 2 is folded back toward the proximal end of the sheath 2 so as to be substantially parallel to the axis of the sheath 2, passes outwardly in the radial direction of the balloon 3 (i.e., on the outer peripheral face thereof) along the axial direction of the sheath 2, and is fixed to the sheath 2 more towards the proximal end than the balloon 3.

Thus, a portion of the reference member 4 projecting from the sheath 2 is moved in conjunction with the expansion of the balloon 3 and enlarges outwardly in the radial direction of the sheath 2, thereby, as described below, moving the reference member 4 so as to be drawn towards the distal end of the sheath 2 by the balloon 3.

As long as the reference member 4 is fixed so that it passes a central portion, in the axial direction of the insertion portion 2, on the outer peripheral face of the balloon 3, at which the diameter takes a maximum value during expansion, the reference member 4 may be folded back in a direction which is not parallel with the axial direction of the sheath 2. This is because the reference member 4 can move in a good correlation with the increase in the diameter of the balloon, and thus measurement of an inner diameter can be performed. For example, while turning the reference member 4 through 180 degrees about the axis of the sheath 2, the first end portion 4A may be fixed on the outer peripheral face of the sheath 2 in a side opposite to the side in which the first lumen 6 is opened.

Figure 3:
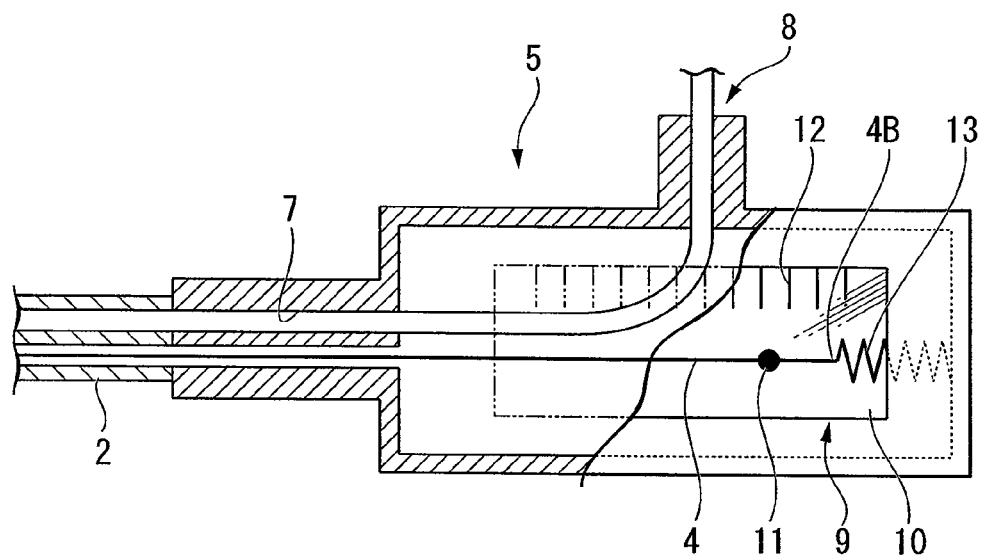
FIG. 3 is an enlarged view depicting a partial cross section of an operating portion of the internal diameter measurement device.

FIG. 3 is an enlarged view depicting a partial cross section of the operating portion 5. The operating portion 5 has a supply port 8 to supply fluid to the balloon 3 and a measuring portion 9 to confirm the position of the proximal end of the reference member 4.

The proximal end of the second lumen 7 opens in the supply port 8 and fluid can be supplied to the balloon 3 by connection with a syringe or the like.

The measuring portion 9 has a transparent visual confirmation window 10 enabling visual confirmation of the reference member 4 therein. A marker 11 is mounted in the vicinity of a second end portion 4B which is a proximal end portion of the reference member 4 to facilitate comprehension of the displacement distance of the reference member 4. The marker 11 may be provided in the second end portion 4B of the reference marker 4, or may be provided at a position separated from the second end portion 4B by a predetermined length, for example by one centimeter.

A graduation 12 which shows the diameter of the balloon 3 corresponding to the displacement distance of the reference member 4 is provided in the measuring portion 9. Thus, the diameter of the balloon 3 can be comprehended by using the graduation 12 to confirm the displacement distance of the second end portion 4B of the reference member 4 or the marker 11.

The second end portion 4B of the reference member 4 is fixed to the proximal end of the measuring portion 9 via a spring (position adjustment member) 13. The spring 13 is adjusted such that the marker 11 is positioned to show a zero diameter value (initial position) on the graduation 12 when the balloon 3 contracts.

An operation upon using the internal diameter measurement device 1 with the above-described configuration will be described.

Firstly, a user inserts an endoscope for industrial or medical use into a pipeline such as a digestive tract or a pipe to measure the internal diameter thereof. The sheath 2 of the internal diameter measurement device 1 is inserted from the forceps port of the endoscope with the balloon 3 contracted. At this time, the position of the marker 11 is adjusted to an initial position by the resilient force of the spring 13.

The distal end of the internal diameter measurement device 1 and the balloon 3 are projected from the distal end of the endoscope. After the balloon 3 is displaced to a measurement position, the user injects a fluid into the balloon 3 from the supply port 8 using a syringe or the like (not shown). The injected fluid is supplied through the second lumen 7 to the inside of the balloon 3 and expands the balloon 3. The user expands the balloon 3 while checking with the endoscope until the balloon 3 makes contact with the inner wall of the pipeline at a central portion of the balloon 3 in the axial direction of the sheath 2 where the diameter of the balloon 3 takes a maximum value.

Figure 4:
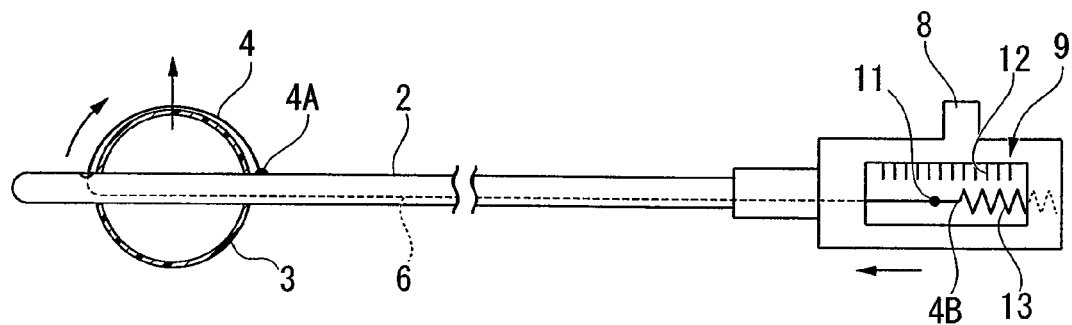
FIG. 4 depicts an operation during use of the internal diameter measurement device.

As the balloon 3 expands and the diameter thereof increases, the reference member 4 is also pressed by the balloon 3 outwardly in the radial direction of the sheath 2 along the outer face of the balloon 3. Since the first end portion 4A of the reference member 4 is fixed to the sheath 2, when the reference member 4 is pressed, the reference member 4 slides in the first lumen 6 as depicted by FIG. 4 and the marker 11 and the second end portion 4B displace towards the distal end of the sheath 2.

The user uses the graduation 12 of the measuring portion 9 to confirm the position of the marker 11 which shows the amount of displacement of the reference member 4 and thus determines the diameter of the balloon 3, that is, the internal diameter of the pipeline at the measurement position.

After completion of measurement operations, the user contracts the balloon 3 by recovering the fluid from the supply port 8 and retrieves the internal diameter measurement device 1 from the pipeline. When the balloon 3 is contracted, the marker 11 is returned to the initial position by the resilient force of the spring 13.

According to the internal diameter measurement device 1 of the present embodiment, since the balloon 3 mounted in the distal end portion of the sheath 2 is mounted so as to encircle the outer periphery of the insertion portion 2, the balloon 3 makes contact with the inner wall of the pipeline across the peripheral direction, the diameter of which is to be measured. Consequently, there are fewer measurement deviations in comparison with the conventional example in which a scale or the like makes contact at two points with respect to the inner cavity of the pipeline. Thus, measurement variability is low and the accuracy of measurements of the internal diameter is improved.

Since the first lumen 6 in which the reference member 4 slides and the second lumen 7 for expanding the balloon 3 are provided separately, when the balloon 3 expands, it is not required to move the reference member 4 and the reference member 4 can slide in the first lumen 6 only as a result of the expansion and contraction of the balloon 3. Thus, change in the diameter of the balloon 3 is more accurately reflected on the displacement amount of the reference member 4 in comparison to a conventional internal diameter measurement device and thus highly accurate measurement of an internal diameter is enabled.

Furthermore, prior to measuring, since the balloon 3 is contracted and has a diameter which is substantially equal to the diameter of the sheath 2, even when the pipeline has an internal diameter which has a relatively small dimensional difference with respect to the sheath 2, no problems arise due to interference by the scale with the inner wall and measurement of the internal diameter is facilitated.

Furthermore, since the diameter of the balloon 3 can be simply comprehended by confirmation using the graduation 12 of the operating portion 5, it is not necessary to use an endoscope or the like for confirmation of the distal end of the internal diameter measurement device 1, which facilitates measurement of the internal diameter.

Furthermore, since the reference member 4 is inserted through the sheath 2, even when the sheath 2 meanders inside the pipeline, the reference member 4 can accompany with the sheath without separation therefrom, and so good measurement of the internal diameter is possible. Furthermore, the overall diameter of the internal diameter measurement device 1 can be reduced into a more compact shape in comparison to providing the cavity for the reference member separately to the sheath 2.

Since the reference member 4 is formed from a material which tends not to expand or contract in the axial direction, when measuring the internal diameter, the reference member 4 does not expand or contract and thus variation on the measurement portion 9 does not tend to occur. Therefore, more accurate measurement of an internal diameter is enabled.

Since the marker 11 is provided in the vicinity of the second end portion 4B of the reference member 4, a user can easily comprehend and measure the amount of displacement of the reference member 4 toward the distal end of the sheath 2.

In addition, since the second end portion 4B of the reference marker 4 is fixed via the spring 13 to the measurement portion 9, when measurement operations are not performed, the marker 11 normally returns to an initial position and thus enables stable measurement operations.

Next, a second embodiment of an internal diameter measurement device according to the present invention will be described making reference to FIG. 5 and FIG. 6. The internal diameter measurement device 21 according to the present embodiment differs from the internal diameter measurement device 1 according to the first embodiment with respect to the shape of the balloon and in that the second end portion of the reference member is free. The same reference numerals are given to the same components as those of the above-described internal diameter measurement device 1, and the descriptions thereof will be omitted.

Figure 5:
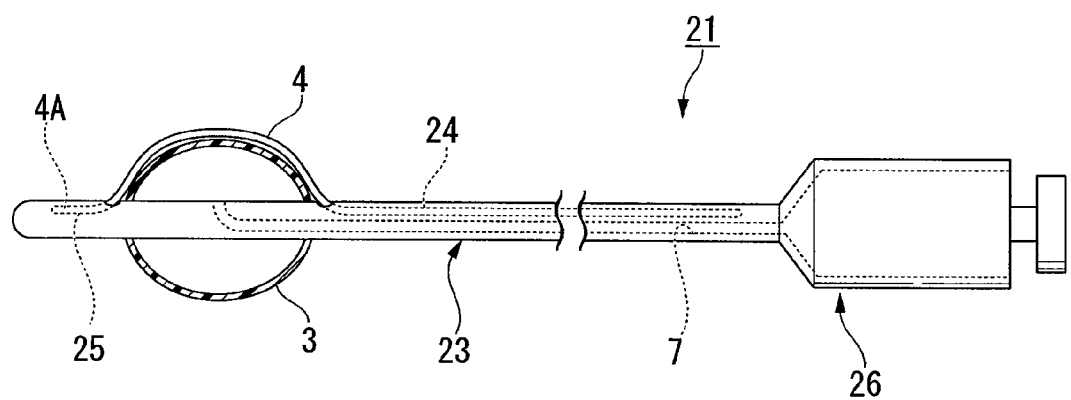
FIG. 5 depicts an internal diameter measurement device according to a second embodiment of the present invention.

FIG. 5 depicts an internal diameter measurement device 21. A first lumen 24 through which the reference member 4 is inserted is opened more towards the proximal end than the balloon 3. The first end portion 4A of the reference member 4 passes outwardly in the radial direction of the balloon 3, is inserted through a fixing lumen 25 provided more towards the distal end of the sheath 23 than the balloon 3, and is fixed thereto.

Figure 6:
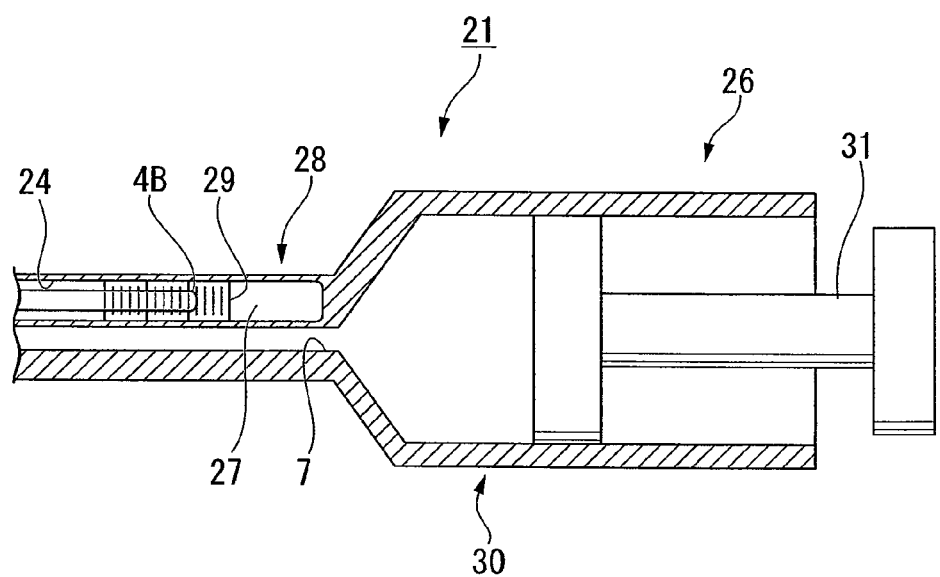
FIG. 6 is a sectional view of an operating portion of the internal diameter measurement device.

FIG. 6 is a sectional view depicting an operating portion 26 of the internal diameter measurement device 21. The second end portion 4B of the reference member 4 is not fixed but rather is free. Thus, the reference member 4 can slide freely in the first lumen 24. A measuring portion 28 with a visual confirmation window 27 is provided in the vicinity of the proximal end portion of the first lumen 24 which thus enables use of a graduation 29 to confirm the position of the second end portion 4B of the reference member 4.

The second lumen 7 is opened in the proximal end of the sheath 2 and a fluid storage portion 30 is provided to hold fluid for supply to the balloon 3. The fluid in the fluid storage portion 30 can be supplied into the balloon 3 and recovered from the balloon 3 with a piston 31.

In the internal diameter measurement device 21 according to this embodiment, the internal diameter of a measurement object such as a pipeline can be measured with high accuracy in the same manner as the internal diameter measurement device 1 according to the first embodiment.

Since the fluid storage portion 30 having the piston is provided in the operating portion 26, measurement of an internal diameter can be performed without separate provision of a syringe or the like.

Next, an internal diameter measurement device according to a third embodiment will be described making reference to FIG. 7 and FIG. 8. The internal diameter measurement device 31 according to the present embodiment differs from the internal diameter measurement device 1 according to the first embodiment in that the first end portion of the reference member is fixed to the balloon. The same reference numerals are given to the same components as those of the internal diameter measurement devices of the above-described embodiments, and the descriptions thereof will be omitted.

Figure 7:
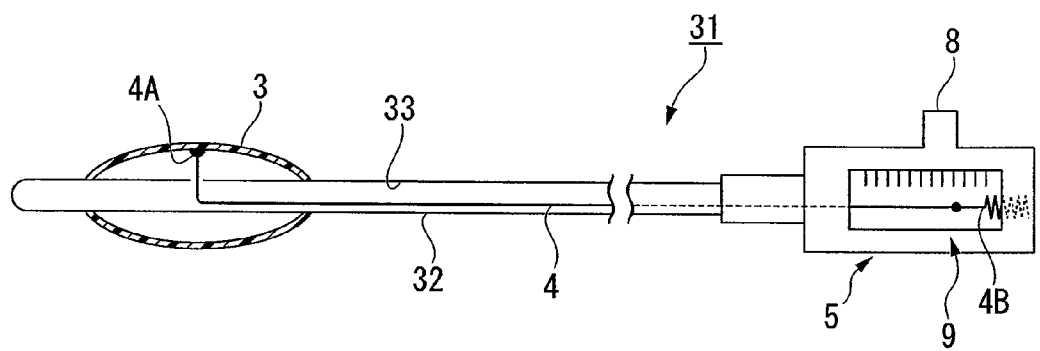
FIG. 7 depicts an internal diameter measurement device according to a third embodiment of the present invention.

FIG. 7 depicts an internal diameter measurement device 31. A sheath 32 has a single lumen (inner cavity) and the reference member 4 is inserted through a lumen 33.

The lumen 33 has an opening into the inner portion of the balloon 3 at a central portion of the balloon 3 in the axial direction of the sheath 32. The first end portion 4A of the reference member 4 projecting from the opening is fixed to the inner face of the balloon 3. The fixed position of the first end portion 4A to the balloon 3 is preferably a single point on an inner peripheral line of the balloon 3 at the central portion in the axial direction of the sheath 32, at which the diameter takes a maximum value when the balloon 3 is expanded. This arrangement enables the radius of the inner diameter of the balloon 3 to be substantially equal to the amount of displacement of the reference member 4 and improves coordination between the balloon 3 and the reference member 4.

Even in the case where the opening position of the lumen 33 deviates slightly from the central portion of the balloon 3 in the axial direction of the sheath 32, measurement of the internal diameter is possible due to the high correlation between the increase in the diameter of the balloon 3 and the amount of displacement of the reference member 4.

An operation upon using the internal diameter measurement device 31 with the above-described configuration will be described.

A user displaces the balloon 3 to a measurement position and injects a fluid using a syringe or the like (not shown) from the supply port 8 in the same manner as the first embodiment. The fluid is supplied to the inner portion of the balloon 3 through the lumen 33.

Figure 8:
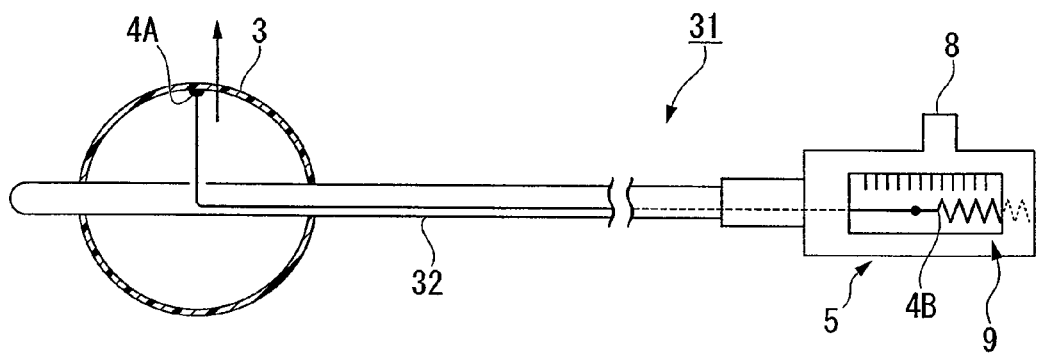
FIG. 8 depicts an operation during use of the internal diameter measurement device.

As depicted in FIG. 8, when the balloon 3 expands, the first end portion 4A of the reference member 4 fixed to the inner face of the balloon 3 displaces outwardly in the radial direction of the sheath 32 and the second end portion 4B displaces toward the distal end of the sheath 32. In the same manner as the first embodiment, the user determines the diameter of the balloon 3 by using the measurement portion 9 to confirm the position of the marker 11 or the like.

In the internal diameter measurement device 31 according to this embodiment, since the reference member 4 is not exposed to the outer face of the balloon 3, the reference member 4 does not make contact with the inner wall of the pipeline. Thus, damage to or severance of the reference member resulting from friction with the inner wall can be prevented.

Since the opening functions both as an opening for allowing projection of the first end portion 4A of the reference member 4 to the outside of the sheath 32 and as an opening for supplying fluid to the balloon 3, it is possible to provide only a single lumen in the inner portion of the sheath 32. This arrangement enables simplification of the structure of the internal diameter measurement device.

When the fluid supplied to the balloon 3 is a liquid, the reduction in friction between the reference member 4 and the lumen 33 enables smooth sliding of the reference member 4 in the lumen 33 and improved measurement of an internal diameter.

Figure 9:
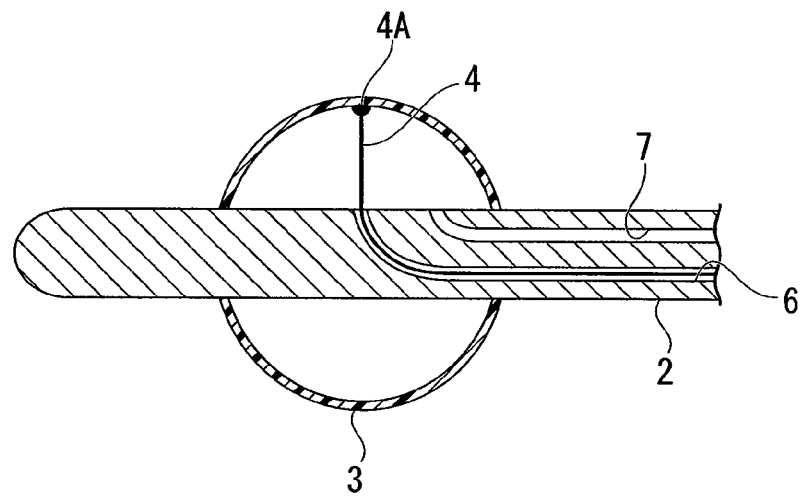
FIG. 9 is an enlarged view depicting a distal end of a sheath and portions proximate thereto in a modified example of the internal diameter measurement device.

In the present embodiment, an example was described in which the sheath 32 included only a single lumen. However, alternatively, as depicted in a modified example in FIG. 9, an internal diameter measurement device may be constituted by using a device provided with two lumens as in the sheath 2 in the first embodiment so as to open a first lumen 6 into the inner portion of the balloon 3

Next, an internal diameter measurement device according to a fourth embodiment will be described making reference to FIGS. 10 to 13. The internal diameter measurement device 41 according to the present embodiment differs from the internal diameter measurement device 1 according to the first embodiment in that a reference member and a measurement portion are not provided. The same reference numerals are given to the same components as those of the internal diameter measurement devices of the above-described embodiments, and the descriptions thereof will be omitted.

Figure 10:
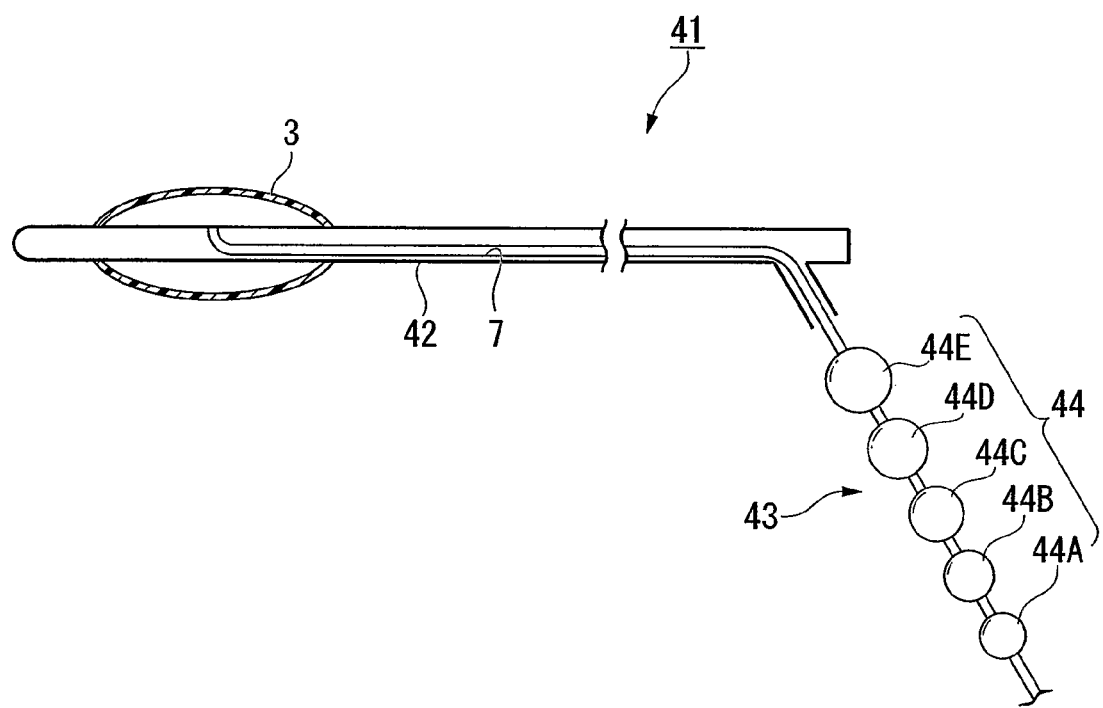
FIG. 10 depicts an internal diameter measurement device according to a fourth embodiment of the present invention.

FIG. 10 depicts an internal diameter measurement device 41. The internal diameter measurement device 41 is provided with a sheath 42, a balloon 3 and a balloon diameter adjustment portion 43 provided on the proximal end of the sheath 42.

The sheath 42 does not include a first lumen 6 and is only provided with a second lumen 7 for supplying fluid to the balloon 3. The second lumen 7 is connected with the balloon diameter adjustment portion 43 in the vicinity of the proximal end of the sheath 42.

Figure 11:
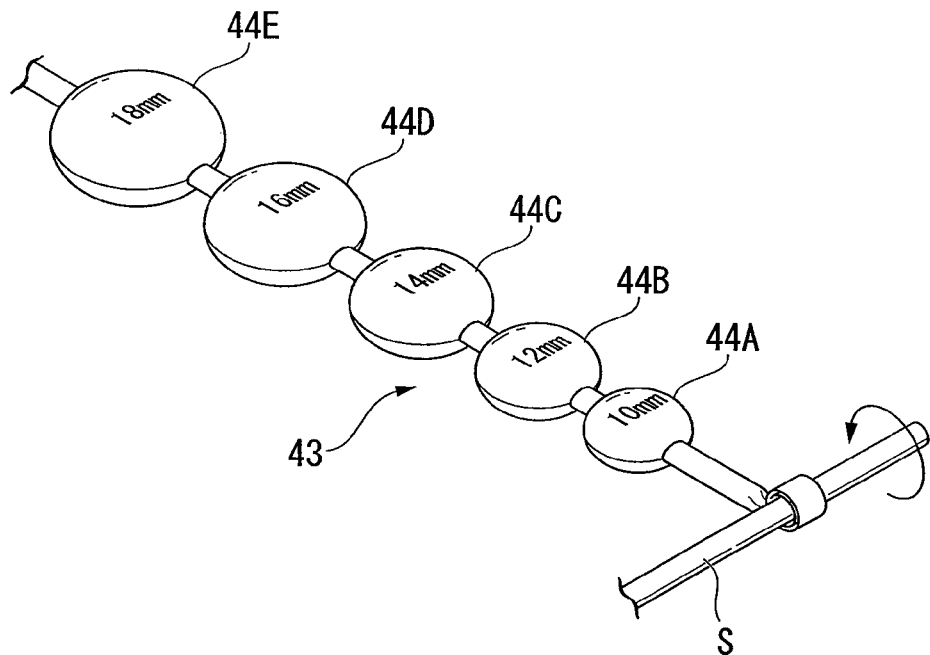
FIG. 11 depicts a balloon diameter adjustment portion of the internal diameter measurement device.

The balloon diameter adjustment portion 43 is formed from a flexible material and includes a plurality of fluid storage chambers 44 filled internally with fluid. As depicted in FIG. 11, the diameter of the corresponding balloon 3 is indicated on respective fluid storage chambers.

An operation upon using the internal diameter measurement device 41 with the above-described configuration will be described.

Firstly, a user inserts the sheath 42 into a pipeline and displaces the balloon 3 to a measurement position. Thereafter, as depicted in FIG. 11, the user applies pressure to the balloon diameter adjustment portion 43 from the proximal end side and supplies internally-stored fluid to the balloon 3. As required, pressure may be applied by rolling the balloon diameter adjustment portion 43 using a bar S or the like as depicted in FIG. 11.

The fluid amount in each fluid storage chamber is set so that, when a fluid up to the distal end of the fluid storage chamber 44A disposed in the most proximal side is applied to the balloon 3 in this manner, the balloon 3 expands to a diameter of 10 millimeters (mm) indicated on the fluid storage chamber 44A. In the same manner, when fluid up to the distal end of the fluid storage chamber 44B is supplied to the balloon 3, the expansion diameter of the balloon 3 takes a value of 12 mm.

By performing this operation, the user can measure the internal diameter of a pipeline by gradually increasing the diameter of the balloon 3 and expanding the balloon 3 until the balloon 3 makes contact with the inner wall of the pipeline. Contact of the balloon 3 with the inner wall of the pipeline may be confirmed by a sensation of resistance when applying pressure onto the balloon diameter adjustment portion 43 or the balloon 3 may be directly observed using an endoscope or the like.

According to the internal diameter measurement device 41 in this embodiment, the amount of fluid supplied to the balloon 3 is adjusted by operation of the balloon diameter adjustment portion 43 and thus the diameter of the balloon 3 can be adjusted to a desired value. Thus, measurement of an internal diameter is enabled without a requirement for a reference member or measurement portion, and this arrangement allows for simplification of the structure of the internal diameter measurement device.

In the present embodiment, an example was described in which the balloon diameter adjustment portion 43 has a plurality of fluid storage chambers 44. However, the shape of the balloon diameter adjustment portion is not limited thereto. An example will be described hereafter.

Figure 12:
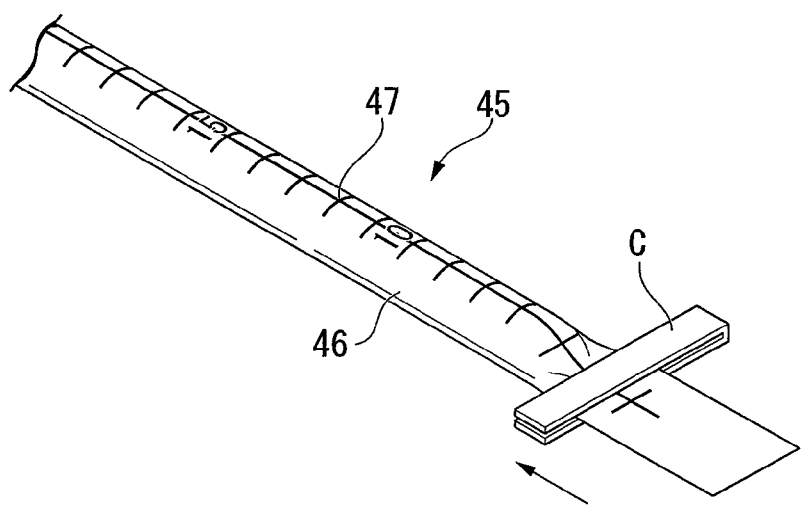
FIG. 12 depicts a balloon diameter adjustment portion in a modified example of the internal diameter measurement device.
Figure 13:
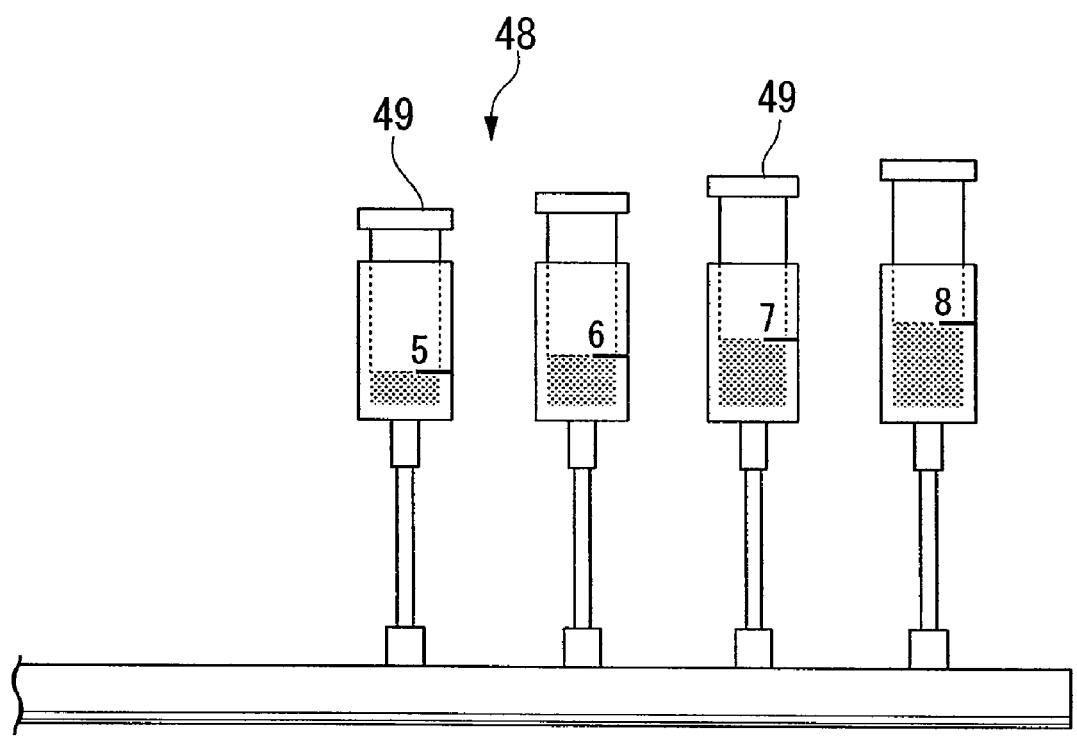
FIG. 13 depicts a balloon diameter adjustment portion in a modified example of the internal diameter measurement device.

FIG. 12 and FIG. 13 both depict balloon diameter adjustment portions of internal diameter measurement devices according to modified examples of the present embodiment. The modified example of a balloon diameter adjustment portion 45 as depicted in FIG. 12 is formed from a linear-shaped container 46 and is structured without a plurality of fluid storage chambers. A graduation 47 is provided on the container 46. The fluid amount is set so that, when arbitrary graduated amount of internally-stored fluid is supplied into the balloon 3 using a clip C or the like, the balloon 3 expands to the diameter corresponding to the gradation. In this manner, the diameter of the balloon 3 can be more precisely adjusted and highly accurate measurement of an internal diameter is enabled.

The modified example of a balloon diameter adjustment portion 48 as depicted in FIG. 13 has a plurality of syringes 49 connected with the second lumen 7. The amount of fluid in each syringe 49 is set so that, by supplying the fluid in each syringe 49 to the balloon 3, the balloon is expanded to the diameter corresponding with the number indicated on the syringe. In this manner, since the diameter of the balloon 3 can be expanded to a desired value by merely pressing a corresponding syringe, the adjustment operation of the balloon diameter can be simplified.

Both balloon diameter adjustment portions may take the object to be measured into account by freely setting the expansion diameter of the balloon corresponding to a syringe, respective fluid storage chambers or the like.

As described above, according to the internal diameter measurement device of the present invention, an internal diameter measurement device which has low measurement variability and which enables accurate measurement regardless of dimension of an object pipeline can be provided.

Furthermore, the invention is not to be considered as being limited by the foregoing description, and is only limited by the scope of the appended claims. Furthermore, additions, omissions, substitutions, and other modifications can be made without departing from the spirit or scope of the present invention.

For example, in the present embodiment, although an example was described in which the reference member was a single linear member, alternatively, a plurality of linear reference members may be inserted into the sheath, passed on the outer peripheral face of the balloon so that the respective reference members are positioned substantially in a radial pattern when viewed from the distal end of the sheath and the first end of each reference member fixed to the sheath. In this manner, more highly accurate measurement of an internal diameter is possible since the increase in the diameter is detected at a plurality of positions on the balloon.

What is claimed is:

1. An internal diameter measurement device configured for insertion into a cavity to measure an internal diameter thereof, the internal diameter measurement device comprising:
    a tubular insertion portion configured to be inserted into the cavity;
    a distending portion which is provided on a distal end portion of the insertion portion, and is configured to be capable of expanding by supplying a fluid to an inner portion thereof;
    at least one linear reference member having a first end portion and a second end portion; and
    a measuring portion which is provided in a proximal end portion of the insertion portion and configured to confirm the position of the second end portion of the reference member,
    wherein the first end portion of the reference member is fixed to the distending portion or the distal end portion of the insertion portion, the second end portion is fixed to the measurement portion, and the second end portion moves towards the distal end of the insertion portion in conjunction with the expansion of the distending portion.

2. The internal diameter measurement device according to claim 1, wherein the reference member is inserted through an inner cavity of the insertion portion in a freely sliding manner in the axial direction.

3. The internal diameter measurement device according to claim 1, wherein the reference member comprises a marker provided in the vicinity of the second end portion and is capable of being visually confirmed in the measurement portion.

4. The internal diameter measurement device according to claim 1, wherein:
    the distending portion is mounted so as to encircle at least a portion of an outer periphery of the insertion portion;
    the reference member projects from the inner cavity of the insertion portion, and passes on an outer peripheral face of the distending portion along the axial direction of the insertion portion; and
    the first end portion is fixed to the insertion portion.

5. The internal diameter measurement device according to claim 1, wherein:
    the distending portion is configured to expand in a spherical shape and is mounted so as to encircle at least a portion of an outer periphery of the insertion portion;
    the inner cavity of the insertion portion has an opening into the inner portion of the distending portion; and
    the first end portion of the reference member projects from the opening of the inner cavity and is fixed on an inner peripheral line of the distending portion at a central portion in the axial direction of the insertion portion.

6. The internal diameter measurement device according to claim 1, wherein the reference member is displaced towards the distal end of the insertion portion as a result of extension of the distending portion.

7. The internal diameter measurement device according to claim 1, wherein the balloon contacts an inner wall of the cavity across the peripheral direction, the diameter of which is to be measured.

* * * * *